(12) United States Patent
Chatterji et al.

(10) Patent No.: US 8,222,230 B2
(45) Date of Patent: Jul. 17, 2012

(54) PHARMACEUTICAL COMPOSITIONS WITH SUPERIOR PRODUCT PERFORMANCE AND PATIENT COMPLIANCE

(75) Inventors: Ashish Chatterji, East Brunswick, NJ (US); Dipen Desai, Whippany, NJ (US); Harpreet Sandhu, West Orange, NJ (US); Navnit Hargovindas Shah, Clifton, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 378 days.

(21) Appl. No.: 12/689,004

(22) Filed: Jan. 18, 2010

(65) Prior Publication Data

US 2010/0184716 A1 Jul. 22, 2010

Related U.S. Application Data

(60) Provisional application No. 61/145,999, filed on Jan. 21, 2009.

(51) Int. Cl.
*A01N 43/04* (2006.01)
*A61K 31/70* (2006.01)

(52) U.S. Cl. .......................... 514/49; 514/43
(58) Field of Classification Search ............. None
See application file for complete search history.

(56) References Cited

U.S. PATENT DOCUMENTS

2007/0202175 A1 8/2007 Ahmed et al.

FOREIGN PATENT DOCUMENTS

WO 2007065829 6/2007

OTHER PUBLICATIONS

Ali et al. Antimicrobial Agents and Chemotherapy (2008), vol. 52, pp. 4356-4369.*
DeFrancesco et al, Nature, (2005) 436:953-960.
International Search Report for PCT/EP2010/050182 dated Jun. 17, 2010.
Ansel et al., Pharm. Dosage Forms & Drug Delivery Systems (1995) pp. 456-457.

* cited by examiner

*Primary Examiner* — Patrick Lewis
(74) *Attorney, Agent, or Firm* — George W. Johnston; Patricia S. Rocha-Tramaloni; Kimberly J. Prior

(57) ABSTRACT

The present invention provides novel formulations of isobutyric acid (2R,3R,4R,5R)-5-(4-amino-2-oxo-2H-pyrimidin-1-yl)-4-fluoro-2-isobutyryloxymethyl-4-methyl-tetrahydrofuran-3-yl ester) and hydroxypropylcellulose that provide high bulk density, low particle size better suited for improved compression and flow, good compression, and fast dissolution profiles.

21 Claims, 8 Drawing Sheets

PHARMACEUTICAL COMPOSITIONS WITH SUPERIOR PRODUCT PERFORMANCE AND PATIENT COMPLIANCE

PRIORITY TO RELATED APPLICATION(S)

This application claims the benefit of U.S. Provisional Application No. 61/145,999, filed Jan. 21, 2009, which is hereby incorporated by reference in its entirety.

BACKGROUND OF THE INVENTION

Isobutyric acid (2R,3R,4R,5R)-5-(4-amino-2-oxo-2H-pyrimidin-1-yl)-4-fluoro-2-isobutyryloxymethyl-4-methyl-tetrahydro-furan-3-yl ester (compound 1) is a hepatitis C virus (HCV) polymerase inhibitor prodrug. Compound 1 can be prepared as described in WO2007/065829. Hepatitis C virus is a blood-borne infectious disease that affects the liver. The infection is often asymptomatic, but once established, chronic infection can cause inflammation of the liver (chronic hepatitis). No vaccine against hepatitis C virus is available.

Compound 1

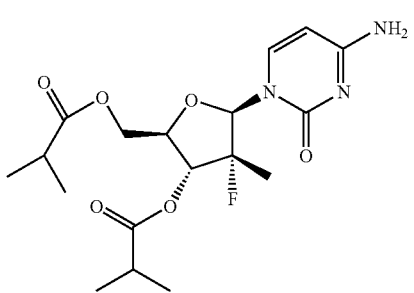

Compound 1 is being evaluated in the clinic for the treatment of liver infection caused by hepatitis C virus. The estimated daily dose is 1 g-2 g requiring high drug loading in the drug product to provide the best treatment regimen for the patients. Compound 1 is a weak base with a pKa of 3.5 thus requiring the drug product to have an immediate release (IR) profile to overcome pH-dependent solubility limitations (see FIG. 1). As shown in FIG. 1, the drug solubility drops precipitously at pH>4 suggesting that the absorption of drug could become dissolution-rate limited at physiologically relevant pH. The high dose and need for an immediate release profile are further complicated by the low bulk density of the drug substance (0.04 to 0.3 g/cc). The conventional manufacturing technologies employing commonly used excipients require the use of multiple densification steps as well as high amounts of excipients such as binders. In addition to the multi-step manufacturing process, the high usage of binder has a negative impact on the dissolution of the product resulting in lower bioavailability.

The availability of commercially manufacturable drug products that provide the best mode of treatment for the patient is a critical component of the drug development process. The safety, efficacy and acceptability of drug can be significantly influenced by the selection of a dosage form that depends on the dose, physico-chemical, and biopharmaceutical properties of the therapeutically active agent. Use of the appropriate manufacturing technologies and pharmaceutically acceptable excipients can resolve many common problems with such compounds. For example, frequently used approaches to resolve the biopharmaceutical issues include technologies such as particle size reduction, lipid solution, conversion to solid dispersions, or the use of amorphous forms. Similarly there are well-established approaches to manage poor particulate properties e.g., flow and compaction properties by mixing with excipients and processing such as granulation and sizing of the particles. Manufacturing technologies such as granulation (dry/wet), fluid bed granulation, and high shear granulation are commonly used approaches to resolve manufacturing difficulties related to flow, content uniformity, and compression. Similarly there are many technologies available to solve poor biopharmaceutical properties of compounds. Although many technologies are available to resolve these issues, the combination of these challenges such as dose, solubility, and poor physico-chemical properties can present insurmountable difficulties in developing suitable products. Accordingly, novel approaches are frequently employed to formulate these products to deliver optimal results with respect to manufacturability, stability, bioavailability, and patient convenience.

SUMMARY OF THE INVENTION

The present invention provides novel formulations of isobutyric acid (2R,3R,4R,5R)-5-(4-amino-2-oxo-2H-pyrimidin-1-yl)-4-fluoro-2-isobutyryloxymethyl-4-methyl-tetrahydro-furan-3-yl ester and hydroxypropylcellulose that provide high bulk density and low granule size better suited for improved compression and flow and fast dissolution profiles.

The present invention provides a composition comprising compound 1 set out below:

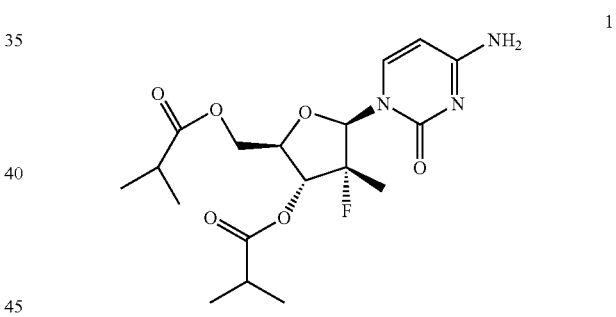

present in an amount from about 50% w/w to about 95% w/w, hydroxypropylcellulose present in an amount from about 1% w/w to about 4% w/w, and at least one excipient present in an amount up to about 49% w/w. The excipient can be selected from the group consisting of compression aids, disintegrants, glidants, lubricants, film-coating agents, and mixtures thereof.

DETAILED DESCRIPTION OF THE INVENTION

Figure 1:
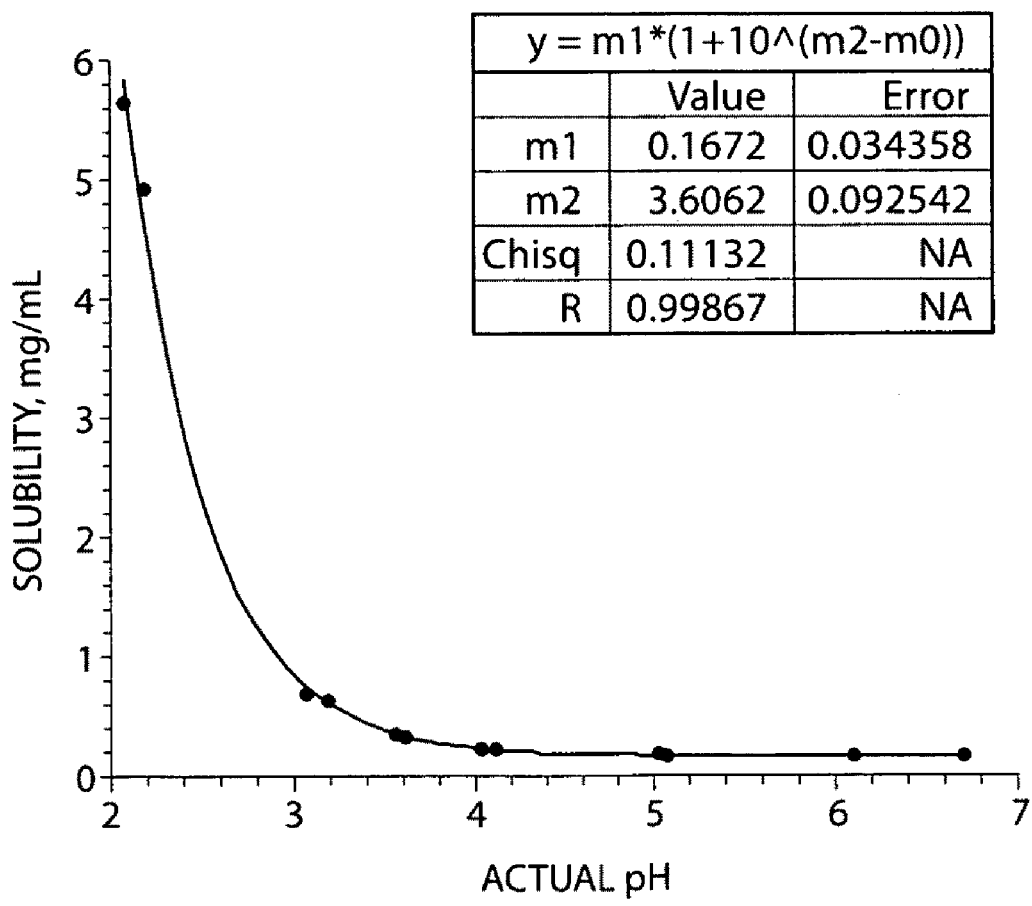
FIG. 1 provides a graph illustrating the pH solubility profile of compound 1 at room temperature.

The present invention provides formulations of compound 1 with hydroxypropylcellulose (HPC) as a binder that resolves many undesirable issues associated with the processing and performance of compound 1 and enables the manufacture of patient friendly dosage forms. The key features of this invention are: (a) the use of hydroxypropylcellulose as a binder at the 1-4% w/w level; (b) the loading of compound 1 at the 50-95% w/w level in the final product; (c) the use of hydroxypropylcellulose as a surface active agent; (d) an overall composition and a process of making the final dosage form; (e) a dissolution profile providing 80% release of the dosage unit of compound 1 in less than 45 minutes and (f) improved bioavailability of compound 1 compared to formulations prepared using alternate methods. The development of suitable dosage forms of compound 1 requires the use of highly functional excipients that can provide the above described attributes of compound 1 at low usage levels. Conventional binders are needed at the 5-10% w/w level in order to provide adequate densification of compound 1, thus decreasing the drug loading of compound 1 in the final product. Surprisingly, for Compound 1, hydroxypropylcellulose provides the required granule density with just a 1-4% w/w level of binder.

As used herein, the following terms have the meanings set out below.

The term "API" refers to the active pharmaceutical ingredient

The term "excipients" refers to an inactive substance used as a carrier for an active pharmaceutical ingredient. Excipients can be used to aid in the absorbtion of the active pharmaceutical ingredient, to bulk up formulations to aid in the manufacturing process, or to help stabilize the active pharmaceutical ingredient. Non-limiting illustrative examples of excipients include antiadherents, binders, coatings, disintegrants, fillers/diluents, flavors and colors, glidants, lubricants, preservatives, sorbents, and sweeteners.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems (6$^{th}$ Ed. 1995) at pp. 196 and 1456-1457.

The term "prodrug" refers to compounds, which undergo transformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The present invention provides compositions comprising compound 1 set out below:

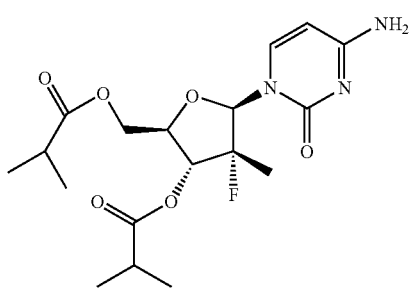

1 present in an amount from about 50% w/w to about 95% w/w, hydroxypropylcellulose present in an amount from about 1% w/w to about 4% w/w, and at least one excipient present in an amount up to about 49% w/w. The excipient can be selected from the group consisting of compression aids, disintegrants, glidants, lubricants, film-coating agents, and mixtures thereof.

As set out above, compound 1 can be present in an amount from about 50% w/w to about 95% w/w, preferably from about 60% w/w to about 90% w/w, more preferably from about 70% w/w to about 85% w/w, and most preferably from about 75% w/w to about 80% w/w.

Hydroxypropylcellulose can be present in an amount from about 1% w/w to about 4% w/w, preferably from about 1.5% w/w to about 4% w/w, more preferably from about 2% w/w to about 3% w/w, and most preferably about 2.5% w/w.

Hydroxypropylcellulose (HPC) is non-ionic water-soluble cellulose ether, formed by reaction of cellulose with propylene oxide. It is soluble in many polar organic solvents and in water below 38° C., but is insoluble in water above 45° C. It has film-forming properties but yields flexibility and adhesion without plasticizers due to its low surface and interfacial tensions of solutions. It has thickening and stabilizing properties and is available in a wide range of viscosities and molecular weights.

Preferably, the compositions of the present invention are in tablet form. A tablet is a mixture of an active pharmaceutical ingredient and excipients (inactive ingredients), usually in powder form, pressed or compacted into a solid. The excipients can include binders (to help hold the tablet together), compression aids, disintegrants (to ensure the tablet breaks up in the digestive tract), glidants (flow aids), lubricants (to ensure efficient tableting), and film-coating agents (to hide the taste of the tablet's components, to make the tablet smoother and easier to swallow, and to make it more resistant to the environment, extending its shelf life). The compressed tablet is the most popular dosage form for an active pharmaceutical ingredient. In the tablet-process, it is important that all ingredients be fairly dry, powdered or granular, somewhat uniform in particle size, and freely flowing. Mixed particle sized powders can segregate due to operational vibrations, which can result in tablets with poor drug or active pharmaceutical ingredient content uniformity.

Compression aids can be present in the inventive composition in an amount up to about 49% w/w, preferably from about 1 to about 40% w/w, more preferably from about 3 to about 20% w/w, and most preferably about 12% w/w. Non-limiting illustrative examples of compression aids include lactose monohydrate, microcrystalline cellulose, starch 1500, and lactose anhydrous. Microcrystalline cellulose is a preferred compression aid.

Disintegrants can be present in the inventive composition in an amount up to about 10% w/w, preferably from about 8 to about 1% w/w, more preferably from about 6 to about 2% w/w, and most preferably about 3.5% w/w. Non-limiting illustrative examples of disintegrants include croscarmellose sodium, crospovidone, starch, cellulose, and low substituted hydroxypropyl cellulose. Croscarmellose sodium is a preferred disintegrant.

Glidants can be present in the inventive composition in an amount up to about 5% w/w, preferably from about 4 to about 0.5% w/w, more preferably from about 3 to about 0.75% w/w, and most preferably about 2% w/w. Non-limiting illustrative examples of glidants include talc, colloidal silicon dioxide, and cornstarch. Talc is a preferred glidant.

Lubricants can be present in the inventive composition in an amount up to about 2% w/w, preferably from about 1.75 to about 0.25% w/w, more preferably from about 1.75 to about 0.5% w/w, still more preferably from about 1.0 to about 0.5% w/w, and most preferably about 0.5% w/w. Non-limiting illustrative examples of lubricants include magnesium stearate, stearic acid (stearin), hydrogenated oil, polyethylene glycol, sodium stearyl fumarate, and glyceryl behenate. Magnesium stearate is a preferred lubricant.

Film-coating agents can be present in the inventive composition in an amount up to about 5% w/w, preferably from about 4 to about 1% w/w, more preferably from about 3 to about 2% w/w, and most preferably about 2.5% w/w. Non-limiting illustrative examples of film-coating agents include hypromellose or polyvinyl alcohol based coating with titanium dioxide, talc and optionally colorants available in several commercially available complete coating systems such as Opadry® film-coating composition (Colorcon) and Advantia® film-coating composition (ISP) or can be produced by mixing individual ingredients.

Opadry® film coating composition (available from Colorcon, Inc.) is a one-step film coating system, which combines polymer, plasticizer and pigment, as required, in a dry concentrate. The coating agent provides film-forming capabilities including sharp logo definition, high tensile strength and adhesion properties. Opadry® is a preferred film coating composition according to the present invention.

Preferred methods for preparing the compositions of the present invention include high shear granulation, low shear granulation, wet granulation, dry granulation, fluid bed drying, milling, blending, compression, and film-coating, fluid bed granulation, roller compaction, and extrusion granulation, with or without the use of granulation fluid. The more preferable modes of granulation are high shear granulation with fluid bed drying and fluid bed granulation, most preferably high shear granulation. Compressed tablets are exerted to great pressure in order to compact the material. If a sufficiently homogenous mix of the components cannot be obtained with simple mixing, the ingredients must be granulated prior to compression to assure an even distribution of the active pharmaceutical ingredient in the final tablet. Two basic techniques are used to prepare powders for granulation into a tablet, wet granulation and dry granulation. Powders that can be mixed well do not require granulation and can be compressed into tablets through direct compression.

High shear granulation is an effective means for turning powders into dense granules for tableting or coating. To create the granules, powders are added to the mixing bowl and the bowl is sealed. If necessary, a dry binder can be added with the powders or dispersed into the granulating liquid. A large impeller spins at desired speeds spinning the powders into a vortex. After the powders are blended together, liquid is added to the product using a pump or pressurized container. A chopper tool located in the bowl spins at fairly high speeds shearing the granules and removing air. The mixing continues until the desired end granule size and density is achieved. End point is often determined via power consumption or torque on the main mixing tool drive. The granulated product can be dried in the mixing bowl, if equipped for vacuum drying, or discharged for fluid bed drying or dried in forced-air ovens.

Wet granulation is a process of adding a liquid binder or adhesive to the powder mixture. The amount of liquid can be properly managed, and over wetting will cause the granules to be too hard and under wetting will cause them to be too soft and friable. Aqueous solutions have the advantage of being safer to deal with than solvents.

Dry granulation is a process used when the product needed to be granulated can be sensitive to moisture and heat. Dry granulation can be conducted on a press using slugging tooling or on a roller compactor commonly referred to as a chilsonator. Dry granulation equipment offers a wide range of pressure and roll types to attain proper densification. However, the process can require repeated compaction steps to attain the proper granule end point.

Fluid bed processing involves drying, cooling, agglomeration, granulation, and coating of particulate materials. It is ideal for a wide range of both heat sensitive and non-heat sensitive products. Uniform processing conditions are achieved by passing a gas (usually air) through a product layer under controlled velocity conditions to create a fluidized state. In fluid bed drying, heat is supplied by the fluidization gas, but the gas flow need not be the only source. Heat can be effectively introduced by heating surfaces (panels or tubes) immersed in the fluidized layer. In fluid bed cooling, cold gas (usually ambient or conditioned air) is used. Conditioning of the gas can be required to achieve sufficient product cooling. Agglomeration and granulation can be performed in a number of ways depending upon the feed to be processed and the product properties to be achieved Direct compression is a method used when a group of ingredients can be blended and placed in a tablet press to make a tablet without any of the ingredients having to be changed. This is not very common because many tablets have active pharmaceutical ingredients, which will not allow for direct compression due to their concentration or the excipients used in formulation are not conducive to direct compression.

Tablet presses, also called tableting machines, range from small, inexpensive bench-top models that make one tablet at a time (single-station presses), no more than a few thousand an hour, and with only around a half-ton pressure, to large, computerized, industrial models (multi-station rotary or eccentric presses) that can make hundreds of thousands to millions of tablets an hour with much greater pressure.

Many tablets today are coated after being pressed. Modern tablet coatings are polymer and polysaccharide based, with plasticizers and pigments included. Tablet coatings must be stable and strong enough to survive the handling of the tablet, and must not make tablets stick together during the coating process. Coatings are necessary for tablets that have an unpleasant taste, and a smoother finish makes large tablets easier to swallow. Tablet coatings are also useful to extend the shelf life of components that are sensitive to moisture or oxidation. Opaque materials like titanium dioxide can protect light-sensitive actives from photodegradation.

TABLE 1

Summary of Product Challenges and Desired Target Product Profile

| Challenges | Target Product Profile |
|---|---|
| High dose (1-2 g/day) for chronic dosing over 3 months | Smallest possible dosage form in easy to swallow format |
| Low solubility at pH >4 | Immediate release profile to take advantage of high solubility in upper gastro-intestinal tract |
| Low bulk density | Simple and robust manufacturing process |
| Bioavailability depends on dosage form composition and process | High bioavailability with low variability |

The compositions of the present invention can be prepared according to the examples set out below. The examples are presented for purposes of demonstrating, but not limiting, the preparation of the compositions of this invention.

EXAMPLES

In accordance with the present invention, the following examples are provided to illustrate preferred methods for preparing compositions of compound 1 with the use of hydroxypropylcellulose as binder at the 1-4% w/w level.

Examples I-III

Conventional Methods for Preparing Compositions of Compound 1

A tablet form was chosen as the preferred dosage form for compound 1. The manufacture of granules is a common practice for densification of the low density of drugs to ensure smooth processing for the tableting process. Several technologies can be used either alone or in combination to achieve satisfactory granulation such as direct powder compression, dry or wet granulation method, and roller compaction or spray granulation methods. The selection of the appropriate granulation process depends upon the properties of the starting materials and the resultant granules such as particle size, density and flow properties because they can have a significant effect on the tablet manufacturing process and can also affect the dissolution. For compound 1, granules with adequate bulk density in the range from about 0.3 g/cc to about 0.6 g/cc, preferably 0.35 g/cc or higher and most preferably 0.4 g/cc or higher are required to achieve adequate powder flow and tighter weight variation during the tableting process. As shown in Table 2, the roller compaction process did not provide adequate densification even at higher roller pressures similarly, direct powder compression was not possible due to the very low bulk density and poor flow property of the active pharmaceutical ingredient. Although adequate densification was not achieved with wet granulation in the early trials, it was selected for further improvement because of superior performance in the early trials.

The manufacture of conventional tablets with commonly used excipients such as binder (povidone), disintegrant (croscarmellose sodium), compression aid (lactose monohydrate and microcrystalline cellulose) and standard manufacturing methods such as high shear granulation, fluid bed drying, milling, compression and film-coating failed to provide tablets with adequate quality particularly with regard to flow properties and weight variations. To improve the manufacturing process, the drug product was manufactured using a higher amount of binder (to obtain higher bulk density) and a dual densification process, i.e., high shear granulation followed by dry granulation (slugging) prior to tablet compression. However, the use of higher binder level and double densification had a negative impact on the dissolution process. Furthermore, this product also required the use of sodium lauryl sulfate as a wetting agent to achieve the binding of the drug as well as aid in the dissolution. The use of sodium lauryl sulfate is not desirable due to unwanted side effects and downstream processing challenges such as poor tablet compression. Based on the initial trials, it was found that the product has not only complex manufacturing process issues but also variable dissolutions.

TABLE 2

Conventional Compositions Evaluated Using Different Granulation Principles

| | Formulation ID | | |
|---|---|---|---|
| | I | II | III |
| | Formulation composition/Principle | | |
| | High shear granulation | Roller compaction (low pressure) % w/w | Roller compaction (high pressure) |
| Compound 1 | 80.0 | 80.0 | 80.0 |
| Filler | 5.0 | — | — |
| Disintegrant | 7.5 | 1.0 | 1.0 |
| Binder | 7.5 | 18.0 | 18.5 |
| Lubricant | — | 1.0 | 1.0 |
| Compression aid | — | — | — |
| Bulk Density | 0.32 | 0.25 | 0.27 |

Examples IV-IX

Effect of Binder Type and Concentration on Compositions of Compound 1

To improve the manufacturing and performance of the product, the wet granulation process was further optimized. Several commercially available binders were evaluated. The following examples set out in Table 3 demonstrate pharmaceutical compositions of compound 1 using different binders.

TABLE 3

Formulations Using Different Binders and Concentrations

| | IV | V | VI | VII | VIII | IX |
|---|---|---|---|---|---|---|
| | | | % w/w | | | |
| Compound 1 | 90.0 | 88.0 | 87.0 | 82.0 | 87.0 | 82.0 |
| Lactose monohydrate | 5.5 | 5.5 | 5.5 | 5.5 | 5.5 | 5.5 |
| Croscarmellose Sodium | 2.5 | 2.5 | 2.5 | 2.5 | 2.5 | 2.5 |
| Hydroxypropylcellulose | 2.0 | 4.0 | — | — | — | — |
| PVP K 30 | — | — | 5.0 | 10.0 | — | — |
| Hypromellose | — | — | — | — | 5.0 | 10.0 |
| Bulk Density (g/cc) | 0.42 | 0.45 | 0.34 | 0.38 | 0.40 | 0.47 |
| Characteristics Granule Diameter ($d_{63.2}$ microns) | 424 | 698 | 574 | 567 | 707 | 1069 |

Figure 2:
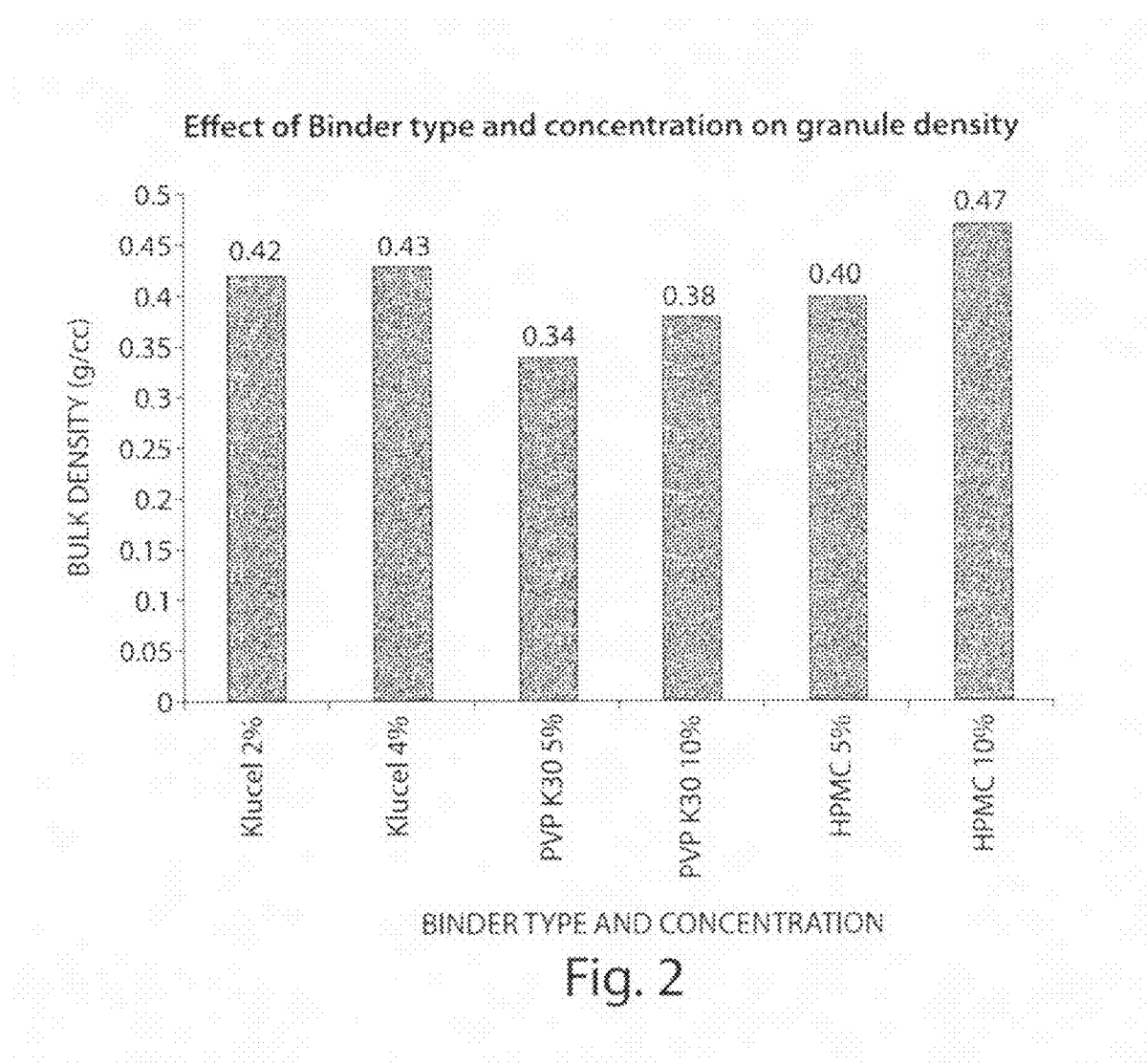
FIG. 2 provides a graph illustrating the effect of binder type and its concentration on bulk density of granulates in compound 1.
Figure 3:
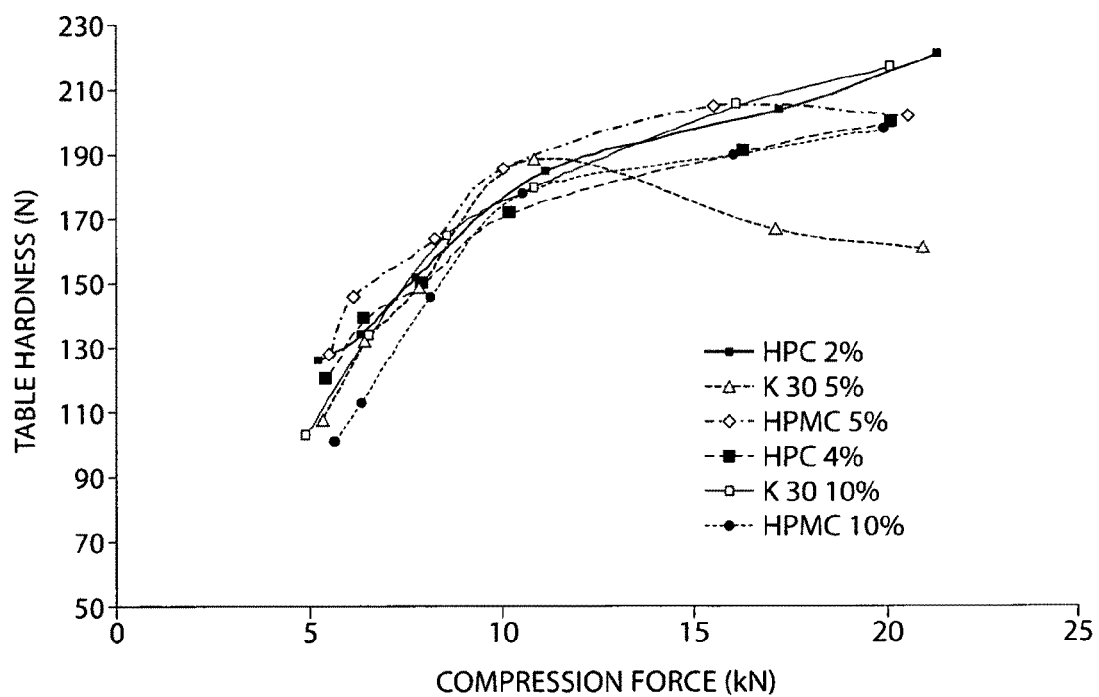
FIG. 3 provides a graph illustrating the effect of binder type and its concentration on compression profiles in compound 1.

The compositions IV to IX were manufactured using conventional wet granulation methods using high shear granulator and fluid bed drying. Binder was added in the dry powder mix and water was used as granulation fluid that was removed during processing. Compression aid microcrystalline cellulose (MCC), glidant (talc), disintegrant (croscarmellose sodium or crospovidone) and lubricant (magnesium stearate) can be added externally to achieve optimized tablet composition. As summarized in Table 3 and shown in FIG. 2, the bulk density of the resulting granules was influenced by the binder type. The increase in bulk density associated with increase in particle size for hypromellose was an expected finding. Similarly no significant influence of polyvinylpyrrolidone (PVP) on the granule size or density is also understandable. However the significant increase in bulk density with hydroxypropylcellulose (HCP, Klucel®, distributed by the Aqualon division of Hercules Incorporated, Wilmington, Del.) with lower granule size was an unprecedented finding. Although hydroxypropylcellulose is a commonly used binder, there is no evidence suggesting the superior densification properties of hydroxypropylcellulose for low bulk density drugs with reasonable granule growth. Furthermore, the formulations manufactured using povidone and hypromellose (HPMC) also exhibited poor compression characteristics perhaps due to under or over granulation (FIG. 3). This effect was attributed to the superior granulation as well as superior compactibility of hydroxypropylcellulose.

Figure 4:
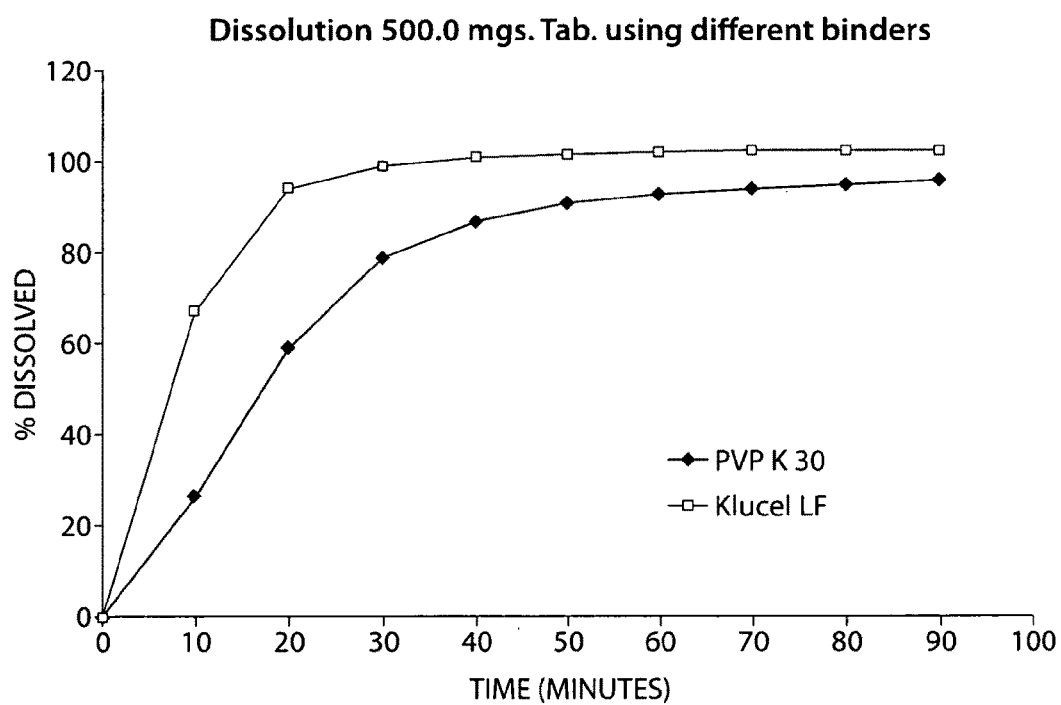
FIG. 4 provides a graph illustrating the effect of binder type and its concentration on in vitro dissolution profile (USP II Apparatus, 37° C., 50 rpm in 1000 mL of 0.005N HCL) in compound 1.
Figure 5:
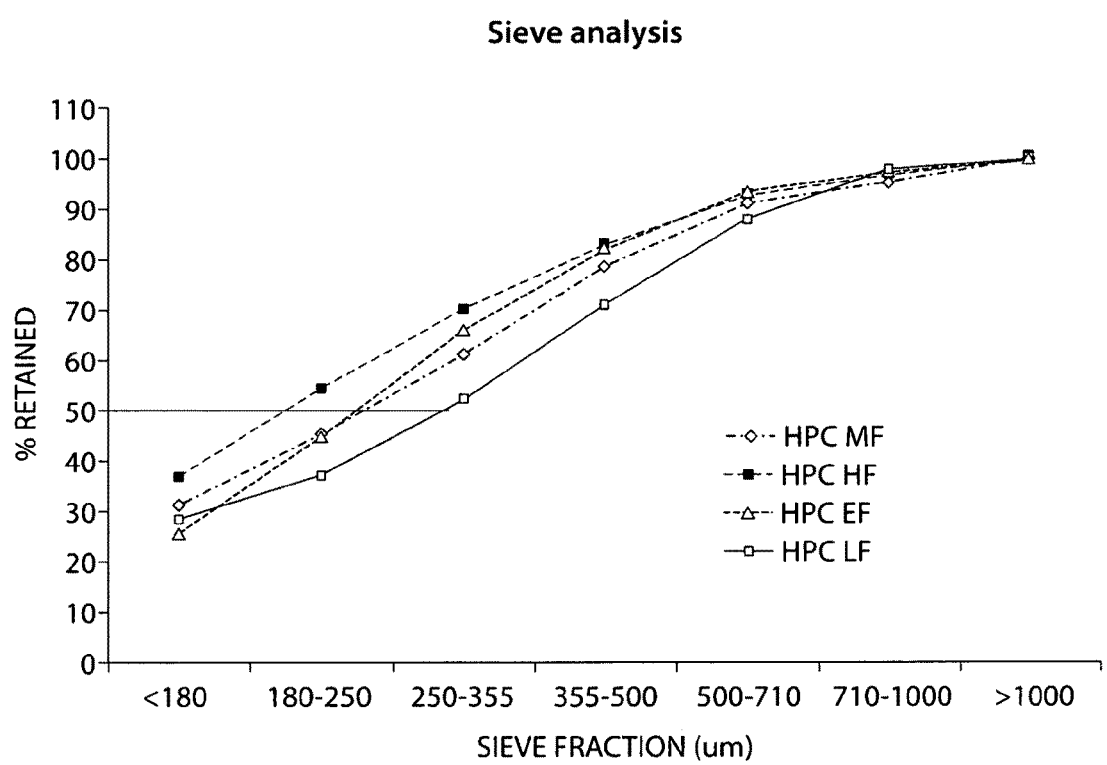
FIG. 5 provides a graph illustrating the effect of hydroxypropylcellulose grade on cumulative granule size, measured using an ATM Sonic Sifter at amplitude setting of 6 for 7 minutes, in compound 1.
Figure 6:
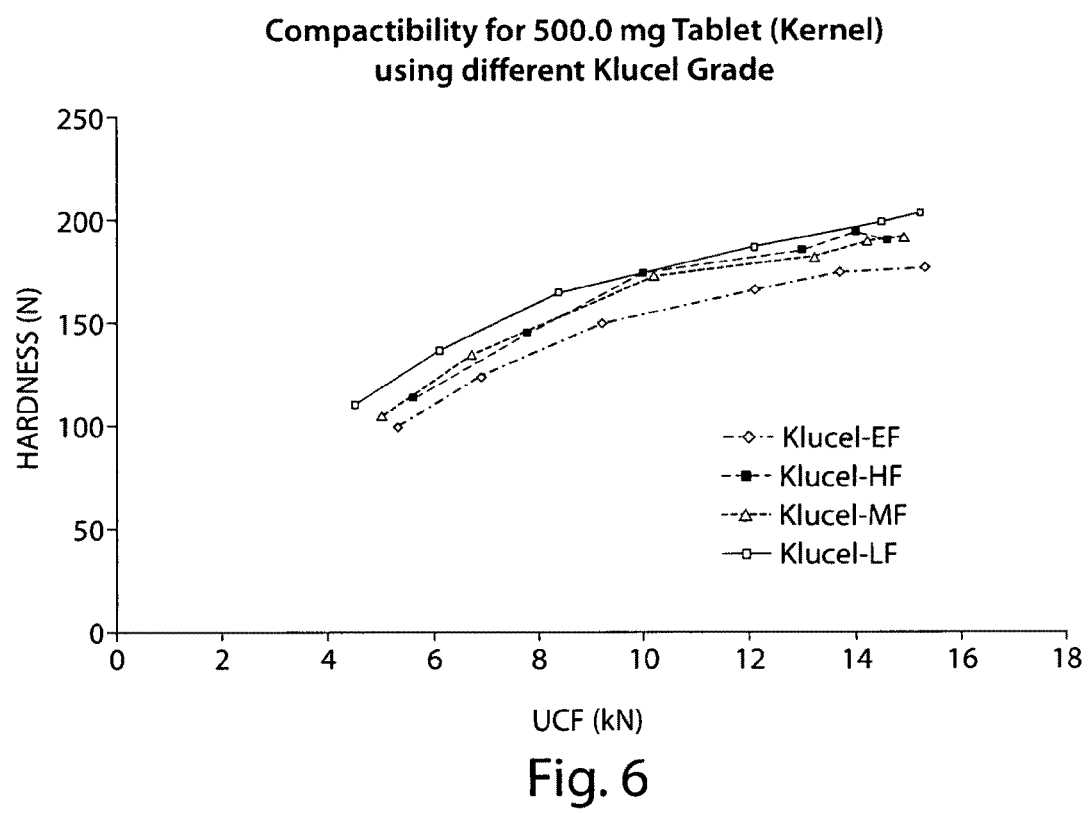
FIG. 6 provides a graph illustrating the effect of different grades of hydroxypropylcellulose on compression profiles, measured using a Presstor®, Compaction Simulator simulating Fette 2090 at 50 rpm, in compound 1.
Figure 7:
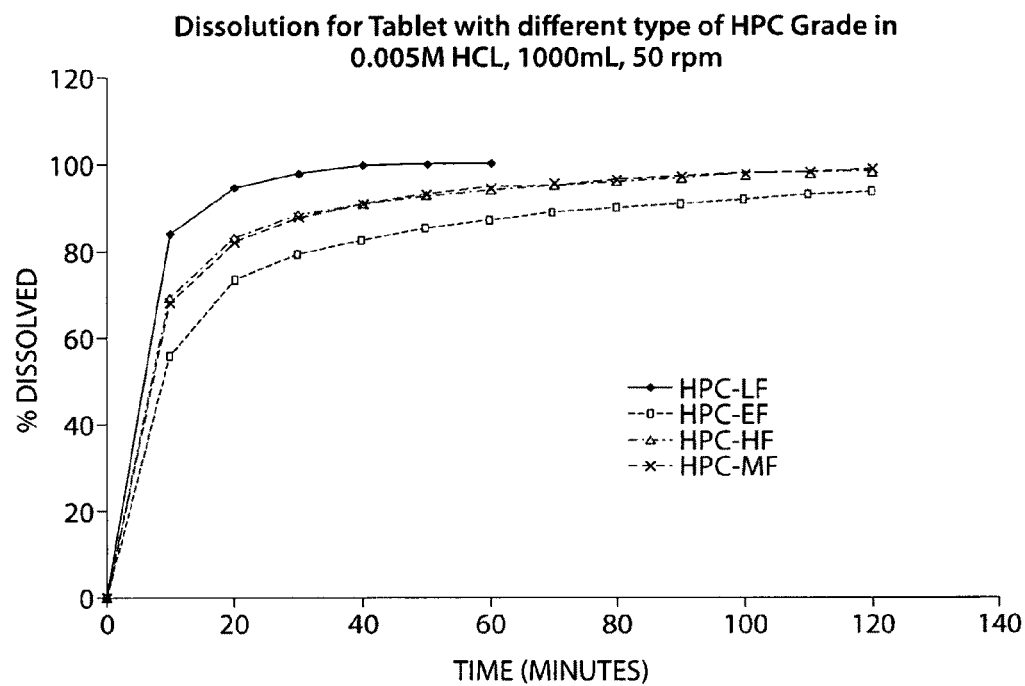
FIG. 7 provides a graph illustrating the effect of different grades of hydroxypropylcellulose on dissolution profiles in compound 1.

This analysis was further extended to evaluate the effect of binder on the dissolution performance of the final dosage form. The tablets were compressed at a desired hardness to a target active weight of 500 mg. The dissolution was studied using USP II dissolution apparatus. As shown in FIG. 4, the dissolution performance of hydroxypropylcellulose formulation was superior to the formulation containing polyvinylpyrrolidone as a binder.

As shown by Examples IV-IX, the use of hydroxypropylcellulose in compositions of compound 1 provides several advantages in ensuring the superior product processing and robustness, for example, (a) higher bulk density; (b) particle size that is better suited for improved compression and flow; (c) good compression; and (d) faster dissolution profiles. In summary, the combination of these advantages with regard to the processing and performance of compositions of compound 1 are unique and could not have been predicted.

Examples X to XIII

Effect of Different Hydroxypropylcellulose Grades on Compositions of Compound 1

To further test the benefits of hydroxypropylcellulose for dosage forms of compound 1, an additional study was designed as set out in Table 4. Four different grades of hydroxypropylcellulose were evaluated, as supplied by Aqualon (Wilmington Del.) as Klucel® LF (HPC-LF, hydroxypropylcellulose-LF), Klucel® EF (HPC-EF, hydroxypropylcellulose-EF), Klucel® HF (HPC-HF, hydroxypropylcellulose-HF), and Klucel® MF (HPC-MF, hydroxypropylcellulose-MF).

Klucel® is provided as a line of hydroxypropylcellulose products that come in a wide variety of viscosity ranges and molecular weights and are distributed by the Aqualon division of Hercules Incorporated, Wilmington, Del.

| Name | Viscosity Ranges (cps)* | Molecular Weight |
|---|---|---|
| Klucel ® EF Pharm | 300-600 (10% w/w) | 80,000 |
| Klucel ® LF Pharm | 75-150 (5% w/w) | 95,000 |
| Klucel ® MF Pharm | 4,000-6,500 (2% w/w) | 850,000 |
| Klucel ® HF Pharm | 1,500-3,000 (1% w/w) | 1,150,000 |

Concentration in water, weight %. Viscosities determined at 25° C., using a Brookfield L VF viscometer
Source: Signet Chemical Corp. Data Sheet. 2002

Compositions X-XIII were manufactured using a conventional high shear wet granulation process. Different grades of hydroxypropylcellulose were added in the dry powder mix and water was used as the granulation fluid that was removed during processing. Compression aid (MCC), glidant (talc), disintegrant (croscarmellose sodium, crospovidone) and lubricant (magnesium stearate) were added externally to achieve optimized tablet composition.

TABLE 4

Effect of Hydroxypropylcellulose Type and Grade on Product Processing and Performance

| | X | XI | XII | XIII |
|---|---|---|---|---|
| Compound 1 | 89.0 | 89.0 | 89.0 | 89.0 |
| Lactose monohydrate | 5.6 | 5.6 | 5.6 | 5.6 |

TABLE 4-continued

Effect of Hydroxypropylcellulose Type and
Grade on Product Processing and Performance

|  | X | XI | XII | XIII |
|---|---|---|---|---|
| Croscarmellose Sodium | 2.7 | 2.7 | 2.7 | 2.7 |
| HPC- LF | 2.7 | — | — | — |
| HPC- EF | — | 2.7 | — | — |
| HPC- HF | — | — | 2.7 | — |
| HPC- MF | — | — | — | 2.7 |
| Bulk Density (g/cc) | 0.42 | 0.50 | 0.45 | 0.44 |
| Characteristics Diameter (d63.2) microns | 424 | 353 | 314 | 368 |

The performance of different grades of hydroxypropylcellulose was assessed using their effect on bulk density of granules, granule size, compression and dissolution while all other parameters were kept constant. As set out in Table 4, the target bulk density of 0.4 g/cc was achieved for all the grades. Some variations were observed between different grades, however it could not be described based on either molecular weight or solution viscosity (as summarized in Table 5). Although all grades were acceptable from a bulk density and particle size perspective, some differences were observed in compression behavior and dissolution. The compression profile with Klucel® EF was on the lower end of acceptability suggesting a higher amount of Klucel® EF can be needed to achieve similar granule properties as with Klucel® LF. Similarly, the lower dissolution of Formulation XI could also be attributed to inadequate binding of the particles. Based on the results, it is evident that all the grades of hydroxypropylcellulose are acceptable in the compound 1 product, but their usage level can need to be optimized with respect to compression and dissolution. Klucel® LF (HPC-LF) is the most preferred hydroxypropylcellulose.

TABLE 5

Different Grades of Binders and Their Molecular Weight
and Solution Viscosity at Different Concentrations

| Polymer | Molecular weight (kDa) | Concentration (% w/v) | Viscosity (mPa s) |
|---|---|---|---|
| PVP K 30 | 30 | 2% | 1.8-3.0 |
| HPMC | 10 | 2% | 2.2-4.5 |
| HPC-EF | 80 | 2% | 6.3-8.0 |
| HPC-LF | 95 | 2% | 15-30 |
| HPC-MF | 850 | 2% | 4,000-6,500 [a] |
| HPC-HF | 1,150 | 1% | 1,500-3,000 [a] |
| PVP K 90 | 90 | 10% | 300-700 [b] |

[a, b] Values quoted from literature.
[a] Aqualon technical bulletin, Klucel ®
[b] Kollidon ® Polyvinylpyrrolidone for the pharmaceutical industry, 8th ed, pp. 22-23.

The preferred hydroxypropylcellulose has a viscosity in the range from about 5 to about 1500 mPa s at a concentration of 1-5% w/w in water at 25° C. with a molecular weight in the range of about 80,000-1,150,000 daltons, most preferable 95,000 daltons.

Examples XIV-XV

Mode of Binder Addition on Compositions of Compound 1

Figure 8:
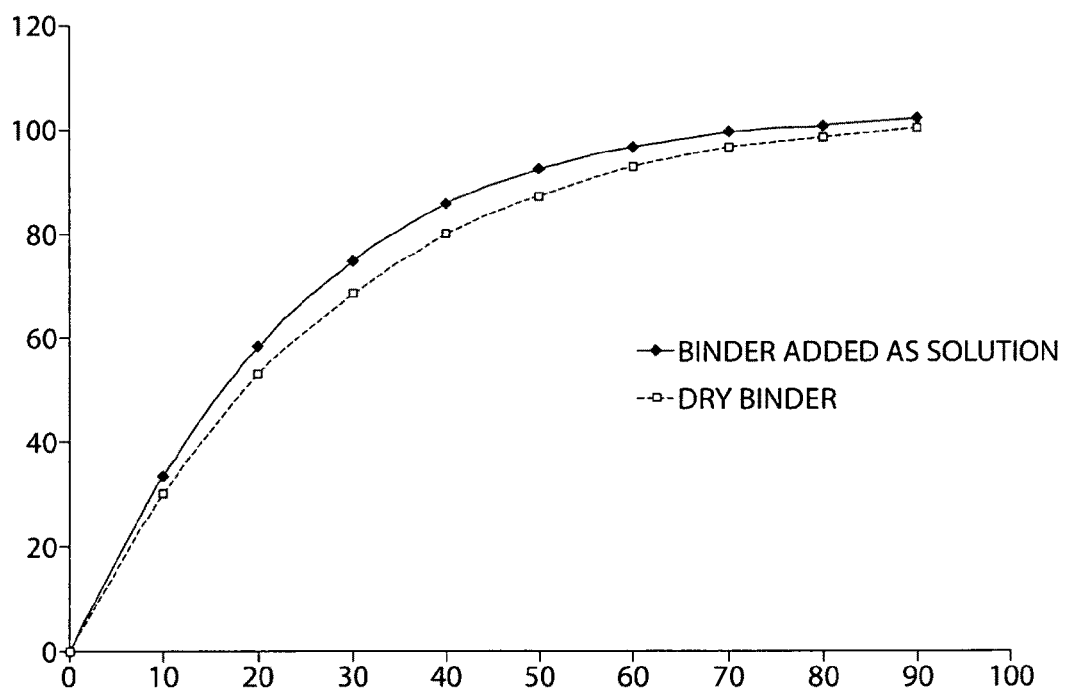
FIG. 8 provides a graph illustrating the effect of binder addition method on dissolution profiles in compound 1.

Examples XIV and XV were prepared to evaluate the effect of the mode of binder addition during wet granulation using the granule bulk density and dissolution profile. As set out in Table 6, similar bulk densities were achieved either by adding binder as a solution or as a dry binder in the powder mass. Moreover, the mode of binder addition appeared to have no effect on the dissolution profile as set out in FIG. 8. Dry binder addition in powder mass is the preferred method because it eliminates the need for a solution preparation step.

TABLE 6

Effect of the Mode of Binder Addition
Method on Compositions of Compound 1

|  | XIV (% w/w) | XV (% w/w) |
|---|---|---|
| Compound 1 | 87.5 | 92.0 |
| Filler (lactose monohydrate) | 8.5 | 6.0 |
| Crospovidone | 2.0 | 2.0 |
| HPC-LF as 5% solution in water | 2.0 | |
| HPC-LF as dry binder in powder mass | | 2.0 |
| Granules Bulk Density(g/cc) | 0.33 | 0.35 |

Examples XVI-XIX

Effect of Concentration of HPC-LF on Compositions of Compound 1

The compositions XVI-XIX show the range of formulations that can be prepared using wet granulation process and compositions to produce tablets of different dosage strengths. Different grades of hydroxypropylcellulose can be added as a binder solution or the dry powder mix and water can be used as a granulation fluid that can be removed during processing. Compression aid (MCC, Starch 1500, reducing and non-reducing sugars), glidant (talc, colloidal silica, silicates), disintegrant (croscarmellose sodium, crospovidone, sodium starch glycolate, corn starch, L-HPC) and lubricant (magnesium stearate, stearic acid, sodium stearyl fumarate, glyceryl behenate) were added externally to achieve optimized tablet composition. The tablets can be coated using standard film-coating compositions such as hypromellose-based coating with titanium dioxide and talc.

TABLE 7

Effect of Concentration of Hydroxypropylcellulose on Compound 1

|  | XVI | XVII | XVIII | XIX |
|---|---|---|---|---|
| Compound 1 | 89.0 | 90.00 | 50.0 | 82.5 |
| Lactose monohydrate | 6.0 | 2.5 | 45.0 | 11.5 |
| Croscarmellose sodium | 2.5 | 2.5 | 2.5 | 5.5 |
| HPC- LF | 2.5 | 5.0 | 2.5 | 2.5 |
| Bulk Density | 0.42 | 0.45 | — | 0.44 |

Examples XXI-XXII

In-Vivo Performance of the Selected Formulations of Compound 1

The pharmaceutical compositions were further evaluated for in-vivo performance in comparison to the formulations described in Table 8. The 'Early formulation' described in Table 8 were manufactured using a 2-step granulation process to achieve target bulk density. These formulations also have sodium lauryl sulfate as the wetting agent to increase wettability and dissolution of the composition to overcome some of the issues for compound 1 described in Table 1. On the other hand, the "Innovative formulation" required only 1-step granulation process to achieve target bulk density. The "Innovative formulation" contains higher API level as well as low binder and disintegrant level compared to "Earlier formulation". The "Innovative formulation" also resulted in smaller tablet (size and weight) due to above mentioned changes.

Later formulations achieved higher AUC (~10%) and $C_{max}$ (~50%) compared to earlier formulations in Monkey studies. Moreover, the $T_{max}$ for the innovative formulations was shorter in monkeys (Table 9). Pharmacokinetic (PK) data from the healthy human volunteer study provided similar observations as reported from the monkey pharmacokinetic study (Table 10). The superior performance of the novel formulations in the pharmacokinetic profile compared to the earlier formulations that contain sodium lauryl sulfate as a wetting agent was also an unpredicted result. Part of that effect can be attributed to the surface-active properties of hydroxypropylcellulose, however, its comparability and superiority to sodium lauryl sulfate as a wetting agent was unexpected. Therefore, the ability of hydroxypropylcellulose to provide better dissolution and bioavailability represents a significant advantage to the product in addition to favorable processing.

TABLE 8

Method of Manufacture and Compositions for Compound 1 Evaluated for in vivo Pharmacokinetic Performance in Monkey and Human Volunteer Studies

| Ingredients | XXI Early formulation % w/w/tab | XXII Innovative formulation |
|---|---|---|
| Compound 1 | 73.5 | 77.0 |
| Povidone K30, | 5.9 | — |
| Klucel ® LF | — | 2.3 |
| Sodium lauryl sulfate | 0.9 | — |
| Croscarmellose sodium | 6.9 | 3.8 |
| Microcrystalline cellulose | 8.8 | 12.3 |
| Colloidal silicon dioxide | 1.0 | — |
| Talc | — | 1.8 |
| Magnesium stearate | 1.0 | 0.5 |
| Coating composition | | |
| Opadry Yellow 03K 12429 | 2.0 | 2.3 |
| Manufacturing Method | Used multistep processing to achieve target granules bulk density | 1 step process: wet granulation provided target granules bulk density |

TABLE 9

Comparative Mean Pharmacokinetics of Compositions of Compound 1 Obtained after Single Dose Administration to Fed Male Cynomolgus Monkeys

| | Dose | |
|---|---|---|
| Formulation | 500 mg tablet Early Formulation (Wet Granulation/Slugging) | 500 mg tablet Innovative Formulation (Wet Granulation) |
| $C_{max}$ (μg/mL) | 6.0 (2.6) | 9.1 (3.7) |
| $AUC_{0-24\,h}$ (μg · h/mL) | 60.2 (27.1) | 67.7 (18.2) |
| $T_{max}$ (h) | 7.4 (1.5) | 5.8 (3.8) |

TABLE 10

Comparative Mean Pharmacokinetic of Compositions of Compound 1 Obtained after Single Dose Administration to Healthy Human Volunteer

| | Dose | |
|---|---|---|
| Formulation | 500 mg tablet Early Formulation (Wet Granulation/Slugging) | 500 mg tablet Innovative Formulation (Wet Granulation) |
| $C_{max}$ (μg/mL) | 8.3 (0.65) | 10.1 (0.8) |
| $AUC_{0-24\,h}$ (μg · h/mL) | 56.9 (3.2) | 69.3 (3.9) |
| $T_{max}$ (h) | 1.65 (0.25) | 1.51 (0.23) |

Example XX

Preferred Composition and Method of Manufacture

Based on the evaluation of different binders, their concentrations and mode of addition in the product and in vivo performance, the following formulation compositions are set out in Table 11 below as a preferred embodiment of this invention.

TABLE 11

Preferred Composition and Method of Manufacture for Compositions of Compound 1

| | % w/w | |
|---|---|---|
| Example XX Ingredients | Preferred composition | Range |
| Compound 1 | 77 | 50-95 |
| Microcrystalline Cellulose (MCC) (or suitable compression aid) | 12.0 | 0-49 |
| Croscarmellose Sodium (or suitable disintegrant) | 3.5 | 0-10 |
| Hydroxypropylcellulose (HPC) | 2.5 | 1-10 |
| Talc (or suitable glidant) | 2.0* | 0-5 |
| Magnesium stearate (or suitable Lubricant) | 0.5* | 0-2 |
| Opadry ® Film-coating composition (or suitable film-coating composition)* | 2.5 | 0-5 |
| Preferred method of manufacturing | High Shear aqueous wet granulation, fluid bed drying, milling, blending, compression and film-coating | |

*Complete film-coating composition supplied by Colorcon (PA)

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

The invention claimed is:
1. A pharmaceutical composition comprising compound 1:

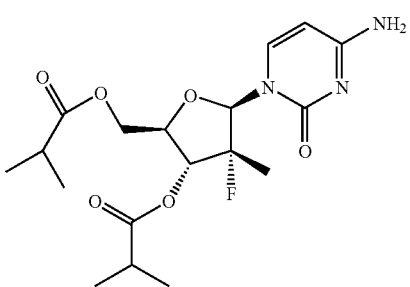

in an amount from about 50% w/w to about 95% w/w, hydroxypropylcellulose in an amount from about 1% w/w to about 4% w/w, and at least one excipient in an amount up to about 49% w/w.

2. The pharmaceutical composition of claim 1, wherein compound 1 is present in an amount from about 60% w/w to about 90% w/w.

3. The pharmaceutical composition of claim 2, wherein compound 1 is present in an amount from about 70% w/w to about 85% w/w.

4. The pharmaceutical composition of claim 1, wherein hydroxypropylcellulose is present in an amount from about 1.5% w/w to about 4% w/w.

5. The pharmaceutical composition of claim 4, wherein hydroxypropylcellulose is present in an amount from about 2% w/w to about 3% w/w.

6. The pharmaceutical composition of claim 1, wherein the excipient is selected from the group consisting of compression aids, disintegrants, glidants, lubricants, film-coating agents, and mixtures thereof.

7. The pharmaceutical composition of claim 6, wherein the compression aid is selected from the group consisting of lactose monohydrate, microcrystalline cellulose, starch 1500, and lactose anhydrous.

8. The pharmaceutical composition of claim 7, wherein the compression aid is present in an amount up to about 49% w/w.

9. The pharmaceutical composition of claim 6, wherein the disintegrant is selected from the group consisting of croscarmellose sodium, crospovidone, starch, cellulose, and low substituted hydroxypropyl cellulose.

10. The pharmaceutical composition of claim 9, wherein the disintegrant is present in an amount up to about 10% w/w.

11. The pharmaceutical composition of claim 6, wherein the glidant is selected from the group consisting of talc, colloidal silicon dioxide, and corn starch.

12. The pharmaceutical composition of claim 11, wherein the glidant is present in an amount up to about 5% w/w.

13. The pharmaceutical composition of claim 6, wherein the lubricant is selected from the group consisting of magnesium stearate, stearic acid, hydrogenated oil, polyethylene glycol, sodium stearyl fumarate, and glyceryl behenate.

14. The pharmaceutical composition of claim 13, wherein the lubricant is present in an amount up to about 2% w/w.

15. The pharmaceutical composition of claim 6, wherein the film-coating agent is selected from the group consisting of hypromellose or polyvinyl alcohol based coating with titanium dioxide and talc.

16. The pharmaceutical composition of claim 15, wherein the coating is present in an amount up to about 5% w/w.

17. The pharmaceutical composition of claim 1, wherein the composition is in granular form and has a bulk density of about 0.35 g/cc or higher.

18. The pharmaceutical composition of claim 1, wherein the hydroxypropylcellulose has a viscosity in the range from about 5 to about 1500 mPa s at a concentration of 1-5% w/w in water at 25° C. with a molecular weight in the range of about 80,000-1,150,000 daltons.

19. The pharmaceutical composition according of claim 1, wherein:

| Ingredient | Range % w/w |
| --- | --- |
| Compound 1 | 50-95 |
| Microcrystalline cellulose | 0-49 |
| Croscarmellose Sodium | 0-10 |
| Hydroxypropylcellulose | 1-10 |
| Talc | 0-5 |
| Magnesium stearate | 0-2 |
| Hypromellose/polyvinyl alcohol Film-coating composition. | 0-5 |

20. The pharmaceutical composition of claim 19, wherein:

| Ingredient | Composition % w/w |
| --- | --- |
| Compound 1 | 77.0 |
| Microcrystalline cellulose | 12.0 |
| Croscarmellose Sodium | 3.5 |
| Hydroxypropylcellulose | 2.5 |
| Talc | 2.0 |
| Magnesium stearate | 0.5 |
| Hypromellose/polyvinyl alcohol Film-coating composition. | 2.5 |

21. The pharmaceutical composition of claim 1 in tablet form.

* * * * *